United States Patent [19]

Hirt et al.

[11] Patent Number: 4,630,729

[45] Date of Patent: Dec. 23, 1986

[54] PACKAGE, FOR EXAMPLE, FOR SURGICAL INSTRUMENTS AND PRODUCTS

[75] Inventors: Edmund Hirt, Stuttgart; Dietmar Send, Memmingen; Günter Diete, Buchenberg, all of Fed. Rep. of Germany

[73] Assignee: Firma Dixie Union Verpackungen GmbH, Kempten, Fed. Rep. of Germany

[21] Appl. No.: 754,274

[22] Filed: Jul. 12, 1985

[30] Foreign Application Priority Data

Jul. 27, 1984 [DE] Fed. Rep. of Germany ....... 3427702

[51] Int. Cl.$^4$ ...................... B65D 43/02; B65D 81/18
[52] U.S. Cl. .................................... 206/363; 156/291; 206/438; 206/813; 229/48 T
[58] Field of Search ................ 156/291; 206/438–441, 206/634, 363, 813; 229/48, 5 B, 48 T; 428/198, 195, 200

[56] References Cited

U.S. PATENT DOCUMENTS

| 3,217,871 | 11/1965 | Lee | 206/440 |
| 3,343,541 | 9/1967 | Bellamy | 206/438 |
| 3,410,393 | 11/1968 | Lee | 206/363 |
| 3,457,919 | 7/1969 | Harbard | 428/195 |
| 3,478,868 | 11/1969 | Nerenberg et al. | 206/439 |
| 3,496,059 | 2/1970 | Rasmussen | 428/198 |
| 3,735,918 | 5/1973 | Tundermann | 229/48 SB |
| 3,827,625 | 8/1974 | Miller | 229/48 SB |
| 3,846,205 | 11/1974 | Yazawa | 156/291 |
| 3,885,074 | 5/1975 | Chandler | 428/200 |
| 4,057,144 | 11/1977 | Schuster | 206/439 |
| 4,139,613 | 2/1979 | Hefele | 156/291 |
| 4,192,448 | 3/1980 | Porth | 229/48 SB |
| 4,226,903 | 10/1980 | Gottung et al. | 428/195 |
| 4,451,520 | 5/1984 | Tecl | 428/198 |
| 4,555,022 | 11/1985 | Eagon et al. | 206/441 |

FOREIGN PATENT DOCUMENTS

| 0021062 | 2/1936 | Australia | 156/291 |
| 0697750 | 11/1964 | Canada | 206/440 |
| 2100259 | 3/1972 | France | 156/291 |

Primary Examiner—William Price
Assistant Examiner—Jimmy G. Foster
Attorney, Agent, or Firm—Holman & Stern

[57] ABSTRACT

The package consists of a strip of plastics foil or sheeting and a strip of paper, whereby the two strips are sealed together at their margins, so as to permit opening by a peeling action. The seal consists of two groups of sealing elements. The sealing elements of group 1 are of small dimensions and ensure "sealability", while the sealing elements of group 2 are linear having a restricted width and which are arranged such that they run transversely to the direction of peel. The arrangement combines a high degree of mechanical strength with ease of peeling during which the tearing-out of fibres from the packaging is minimized.

7 Claims, 4 Drawing Figures

U.S. Patent  Dec. 23, 1986  4,630,729
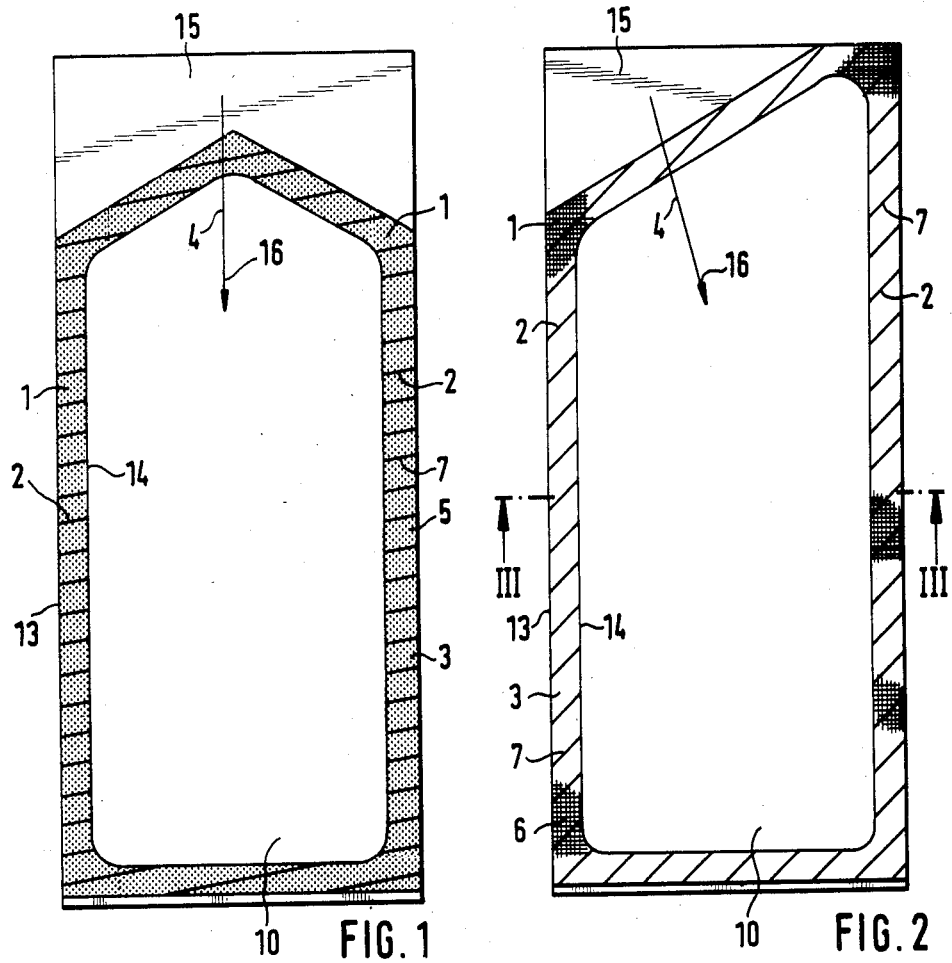
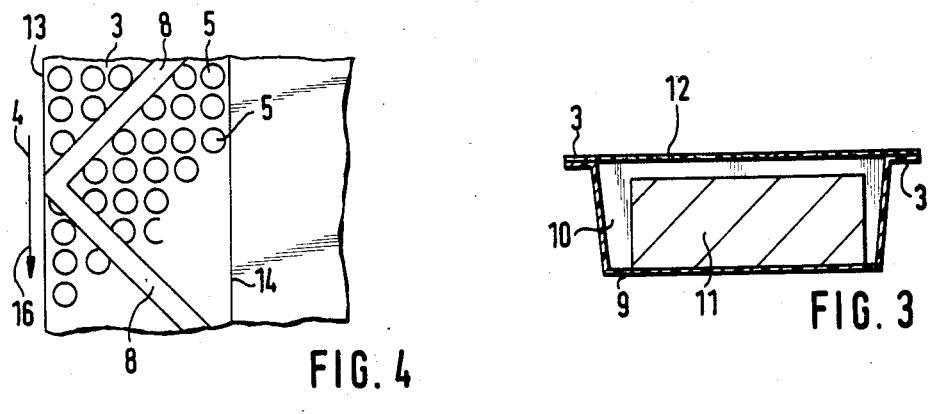

PACKAGE, FOR EXAMPLE, FOR SURGICAL INSTRUMENTS AND PRODUCTS

BACKGROUND OF INVENTION

The invention relates to a package, for example, for surgical instruments and products, formed from a strip of plastics and a strip of paper or the like.

It is well known, for example, for surgical instruments, syringes, catheters and similar to be sterile-packed, in order to ensure that at the moment of use of the packed goods sterilisation does not have to be carried out. Moreover, this ensures that the packed goods are destined for single use only (disposed of after use), since it is on this premise alone that an optimum in terms of sterility can be achieved by this method.

After packing the goods, which as a rule is effected without the use of vacuum, the finished packages are subjected to a sterilisation process. The application of heat corresponding to the temperature of steam, i.e. the use of heat for sterilisation is not particularly favoured, because the necessary heat can have a disadvantageous affect upon both the component elements of the package as well as upon the packed items. For example, the strip plastic adopted or the plastic components of the packed goods soften at the sterilisation temperature. For many medicines, syringes or corresponding products the use of elevated temperatures is out of the question.

Sterilisation is effected, therefore, by gassing with a germicidal gas. For this purpose, the packages are placed in an enclosed container and the air within the packages is replaced to an adequate degree by the germicidal gas introduced into the container by alternate application of a partial vacuum and superatmospheric pressure.

The process of gas exchange is achieved by the fact that the strip paper of the package is such as to allow the gas to permeate through, whilst possible germs are retained by the strip paper.

The residual quantities of gas provide adequate protection against renewed bacterial contamination until the packages are used or consumed, assuming the package is adequately sealed.

It now presents no problem to join the strip of paper and the plastic foil sheeting together, preferably by sealing in a manner in order to ensure an adequate level free from leakage. The edge to which the two strips of foil sheet are joined together for each package, has to have a suitable width for this, whereby, as a rule, approx. 5 millimeters is considered sufficient. By a suitable sealing operation which is usually made on the application of heat and whereby a sealing tool presses the edge on one side against a support, which is arranged on the other side, a tight seal can be easily accomplished.

When a package of this type is to be opened, it should be possible to do so without the use of additional tools, and it is required to be able to peel off the strip of plastic foil and the strip of paper from each other, for which, if need be, a tab or another projection is used for the opening operation.

The condition of this so-called ability to peel presupposes that the bond between the two component part of the package is not too firm. If the seal or similar is bonded too tightly, the strip of paper will not peel off, adversely affecting the opening operation.

In addition, in peeling the two sheet materials apart, there is the problem that fibres and lumps of fibre will be torn out of the strip paper in the event of the bond being too strong, possibly causing the fibres to fall on the packed goods, i.e. the surgical instruments, which following operations, can lead, for example, to inflammation and other undesirable consequences for the patient. Therefore, the bond between the strip paper and the strip of foil sheeting is to be made such that, on the one hand, the peelability is retained, and, on the other hand, no loose fibres occur during peeling.

However, in so doing, attention must be paid to the fact that the strip paper is made in such a manner that it is basically gas-permeable, which virtually excludes the use of agents which are suitable for increasing the cohesion of the fibre-bond of strip paper. Such agents, like glue or similar, which are otherwise used to increase the strength of the fibre bond of the material would have a disadvantageous affect upon the penetration of gas.

A reduction of the bonding effect of the sealing between the two strips now has the result that during the above described gas exchange, in which the package is subjected to repeated suction, on which the package inflates, the seal is adversely affected, i.e. that the package will become unsealed. Such unsealed packages can be difficult to detect externally.

When mention is made in the preceding and following text regarding the seal in context with the bond of the strip paper with the plastic foil sheeting, this is not taken as a limiting concept. As a rule, sealing is indeed used, but it is also possible to replace the sealing by an adhesive operation. Even bonding agents, which are considered superior to "welding", can be adopted.

This means with which the effect of a sealed seam is intensified or lessened is known per se. A proposal was made for a package of a similar type in the specification of West German patent application No. DE-AS 26 08 777, but was for resolving another object being that the welding base bearer which operates in conjunction with the sealing tool is designed such that it features a plurality of pyramid-shaped raised projections, thus producing a seal for which the individual elements of the seal consist of a plurality of spots.

Furthermore, it is also intimated in the above mentioned document the use of a welding base which has a plurality of pyramid-shaped depressions, so that the sealing elements between the two strips receive a net-like form. The adoption of the described welding base is made in the mentioned document for the purpose of avoiding adhesion of the package to the welding base. However, it has been found that in using the mentioned means, when the elongations of the individual sealing points or lines remain sufficiently small, the bonding effect of the seal is limited, such that a good "peelability" is achieved.

It is further known to seal the edge of the packages in question so that several seams are arranged on the edge, whereby the sealing seams then surround the formed receptive cavity as the case may be. The use of a plurality of such linear sealing seams running parallel to the edge increases "sealability" and improves the bond as well between the two strips. On peeling one of the strips from the other, however, it unavoidably results in a tearing out of the fibres of the strip paper, with all the disadvantageous consequences.

SUMMARY OF THE INVENTION

It is the object of the invention to improve a package of the type referred to the effect that, on the one hand, the absolute "sealability" and the mechanical cohesion of the two strips remains assured, and that, on the other hand, the two strips can nevertheless be easily peeled from each other without the danger of releasing fibres from the strip of paper.

To resolve this task the invention provides a package for example for surgical instruments and products formed from a strip of plastics foil and a strip of paper or the like in which and whereby the two strips of material which surround a cavity are joined by being sealed together, having a projection region for an opening operation, in which the strips may be peeled apart along the edge, wherein the bonded edge to be opened has at least two uniformly distributed groups of bonding elements, of which the first group is of relatively small dimensions in at least one direction in the plane of the edge, and of which the second group consists of considerably longer lines of limited width, whereby the lines are arranged such that they basically run transversely to the predetermined direction of peel.

The invention is based upon the concept that basically, there is no significant additional expenditure if various sealing elements are adopted for joining the two strips. The sealing elements are obtained by the fact that either the sealing bars or the welding base or counterbars for this, or, both bars, feature a suitable surface, which ensures that the appropriate sealing elements on the package are produced in the desired form, and, as a result, produce the desired effect. In this context, it is an important fact that it is necessary to design the arrangement such that any desired shapes of packages can be produced. The sealing bars and the counter-bearers for this can be manufactured for the invention without further ado, as plate-like blanks, from which the chosen forms can then be made, which are matched to the corresponding package forms.

If it is not possible to effect manufacture in this manner, it will be necessary to manufacture a certain tool for each type of package or for each size. Since the invention distributes the various sealing elements uniformly, the invention achieves this important advantage.

The invention now proceeds from the concept that the first group of bonding elements is so designed that the "sealability" is guaranteed and the ability to peel assured, as far as these elements are concerned. The first group, in at least one direction, are of small dimensions, such that it is not likely to tear out fibres from the bonded fibres of the paper form, because the forces transmitted from the sealing elements to the fibres are much too limited to overcome the cohesion forces of the fibres in the bonded fibres. Generally, the fibres are considerably longer than the dimensions of these sealing elements is broken, or the fibres, provided that they are small, are indeed pulled out, but retained on the sealing elements.

The second group of bonding elements or sealing elements for the invention now has the task to secure the mechanical cohesion between the two strips. However, since this group does not have, for example, the task of producing an adequate degree of "sealability", this group can be designed accordingly.

This is brought about the fact that the lines only have a limited width, which would not be sufficient to effect a seal. This group of sealing elements can be positioned such that no disadvantageous effects occur on opening. The invention achieves this by the fact that the lines run transversely to the envisaged direction of peel. Were the lines to basically run in the direction of peel, then the line-like sealing elements would tear out rows of fibres or lumps of fibre during peeling. Since the lines are arranged transversely to the direction of pull, only a relatively limited width of the strip paper is affected during peeling. Fibres are indeed pulled out which run virtually parallel to the line if these are sufficiently bonded with the sealing elements. This is not a disadvantage however, because these fibres are not released. Fibres which run transversely to the line are, in contrast, only slightly affected.

It has proved in practice that it is advantageous if the lines do not run exactly at right angles to the direction of peel, but form an acute angle with the direction of peel. This results in a reduction of the tear-out forces during peeling, which, on the one hand, enables the peeling operation to be uniform, and, on the other hand, reduces the danger of the forming of loose fibres.

BRIEF DESCRIPTION OF THE DRAWINGS

Several embodiments of the invention are schematically depicted by way of example in the drawing in which:

FIG. 1 is a plan view on a package formed in accordance with the invention,

FIG. 2 is an alternative embodiment of the invention,

FIG. 3 is a sectional view corresponding to the section line III—III of FIG. 1; and FIG. 4 is a plan view on a part of another embodiment of the invention, to a considerably enlarged scale.

DETAILED DESCRIPTION OF THE INVENTION

The package in FIGS. 1 and 2 consists basically of a bottom sheet 9 made of plastics material in which the beaker-like receptive cavity 10 is formed. This receives the items 11 (not shown) to be packed. A cover sheet 12 placed thereon consists of paper or a paper-like material. On the surrounding, margins 3 the sheets 9 and 12 are bonded with each other to form a joined region, preferably by sealing. For this purpose, as known per se, a sealing tool and a counter-reacting tool operate together (not shown).

. One or both tools have a structure for achieving the sealing elements, as have been described and to be explained below in detail. Sealing can be achieved by heating one of the tools or even by using other energy forms. Both tools operating together can be hard and comparably rigid, i.e. be designed as metal tools. However, it is also possible to arrange for only the sealing tool to be hard, whilst the counter-tool is relatively flexible. Whether the sealing tool operates from above on to the strip paper or from below on to the plastics sheet is not important.

The margins 3 are bordered in the example by parallel contours 13 and 14, whereby the contour 13 basically forms the outer edge of the package, whilst the contour 14 defines the edge of receptive cavity 10. The margins can be the same width all the way around. Generally, a width of approximately 5 millimeters is sufficient. For the embodiments depicted as per FIG. 1 and 2 the margins 3 totally surround the receptive cavity 10 and are basically designed similarly in all parts. The invention can also be adopted if, for example, the lower part of the margins 3 cannot be peeled off, and also insomuch that on opening the package complete separation does not occur.

For the embodiment of FIG. 1 the package can be gripped in the region of a tab zone 15, where the two strips or the bottom sheet and the cover are not bonded together.

The cover sheet i.e. the strip paper, can be peeled off in the direction of the arrow 16.

Since the first group of sealing elements, as shown in FIG. 1, are designed as spots 5, these sealing elements separate easily without the fibre bond of the strip paper being affected. Lines 7 which run transversely to the direction of the arrow 16, indicate the second group of sealing elements which increase considerably the cohesion between the two strips, without tearing out the fibres from the cover 12 during peeling.

The embodiment in accordance with FIG. 2 differs there from the embodiment as per FIG. 1 in that the tab zone 15 is arranged on the side, so that a different direction of peel is effected. In the embodiment as per FIG. 2 the sealing elements of the first group 1 are arranged in the form of a net 6, which has very thin lines.

FIG. 4 shows point-like sealing elements 5 in combination with zig-zag lines 8. The direction of peel 4 is indicated by the arrow 16.

The distance of the points 5 from each other and the size of the points is to be selected such that only a tight seal is achieved, but not a flat seal.

With a distance of the points from each other of less than one millimeter and a point diameter of a size to enable separation, practicable results are attained. The distance of the lines of the net 6 from each other may approximately correspond to the distance of the points 5 from each other. The width of the net sections must, however, be sufficiently limited in order to avoid a flat surface bond which forms effectively a flat surface which could transfer sizable forces.

In contrast to the sealing elements of group 1 the sealing elements 7 and 8 are longer and extend over the width of the edge 3. The width of these sealing elements 7 and 8 should, however, basically not exceed approximately one millimeter.

The zig-zag lines 8 of the embodiment as per FIG. 4 can be, for example, parts of a grid. The corner spots of the zig-zag lines must not repeat on the margin 3.

The invention can also be effected if the sealing elements feature other forms to those indicated. The sealing elements 1 can, therefore, be of an elongated formation instead of circular. The sealing elements of group 2 can even be formed of wavy lines, in which case, care is to be taken to ensure that the part sections do not run parallel to the direction of peel.

We claim:

1. A packaging device for use with products to be sterilized such as surgical instruments and products and the like, comprising: a first sheet of plastics material and a second sheet of flexible material; said second sheet being composed of paper-like material which is composed of single fibers; said first sheet and said second sheet having corresponding marginal portions; said marginal portions of said first and second sheets of material being joined together; a body; said body having a cavity adapted to contain a product; said first sheet being connected to said body adjacent said cavity; said cavity being closed by said second sheet; said second sheet being adapted to permit permeatation of a gas therethrough; said marginal portions which are joined together comprising a joined region; said cavity being bounded by said joined region; at least a portion of said second sheet projecting beyond said joined region to facilitate an opening operation by peeling said joined region apart;

said first sheet and said second sheet having respective confronting surfaces at said joined region; there being disposed upon at least one of said confronting surfaces a first group of bonding elements and a second group of bonding elements; individual elements of said first group each being of a first, small, dimension in at least one direction in a plane of said joined region; individual elements of said second group comprising a narrow elongated line of bonding; each of said individual elements of said second group being disposed generally transversely to a predetermined direction of peeling for an opening operation; whereby said first group of bonding elements is so constructed as to permit separation of said first and second sheets of said joined region readily without substantial pulling out of fibers from said second sheet; and whereby said second group of bonding elements is so constructed as to provide a stronger bond than does said first group of bonding elements, and whereby fibers pulled out from said second sheet by said second group of elements during separation of said joined region are retained by said individual elements of said second group to avoid contamination of the product.

2. A packaging device as claimed in claim 1, wherein the elements of said first group are in the form of spots.

3. A packaging device as claimed in claim 1, wherein the elements of the first group form a reticulate pattern.

4. A packaging device as claimed in claim 1, wherein said individual elements of said second group disposed in a pattern of generally parallel lines.

5. A packaging device as claimed in claim 4, wherein said generally parallel lines are disposed at an acute angle to an edge of said marginal portions.

6. A packaging device as claimed in claim 4, wherein said generally parallel lines are disposed at an angle of approximately 45° to an edge of said marginal portions.

7. A packaging device as claimed in claim 1 wherein said individual elements of said second group are disposed in a pattern of a plurality of wavy lines, which are disposed in a zig-zag pattern.

* * * * *